United States Patent
Fouache et al.

(10) Patent No.: US 6,630,586 B1
(45) Date of Patent: Oct. 7, 2003

(54) BRANCHED MALTODEXTRINS AND METHOD OF PREPARING THEM

(75) Inventors: Catherine Fouache, Sailly Labourse (FR); Pierrick Duflot, Lacouture (FR); Philippe Looten, Lambersart (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/455,009

(22) Filed: Dec. 3, 1999

(30) Foreign Application Priority Data

Dec. 4, 1998 (FR) ............................................. 98 15344

(51) Int. Cl.$^7$ .............................. C08B 30/18; C07H 1/08
(52) U.S. Cl. ........................ 536/103; 536/124; 514/58; 426/804; 127/38
(58) Field of Search ..................... 127/36–40; 536/103, 536/124; 514/58, 738; 426/48, 804

(56) References Cited

U.S. PATENT DOCUMENTS

| | | | |
|---|---|---|---|
| 4,422,881 A | 12/1983 | Devos et al. ................. | 426/48 |
| 4,445,938 A | * 5/1984 | Vervaerde et al. ............ | 127/29 |
| 4,840,807 A | 6/1989 | Yoshida et al. ............... | 127/38 |
| 5,493,014 A | * 2/1996 | Caboche ..................... | 536/103 |
| 5,837,060 A | * 11/1998 | Fouache et al. .............. | 127/36 |
| 6,306,836 B1 | * 10/2001 | Martis et al. ................. | 514/58 |

FOREIGN PATENT DOCUMENTS

EP 710670 * 5/1996

OTHER PUBLICATIONS

Abstract of food Chemical Codex—Monograph Specifications p. 239–240, 1991.
Article of Hakomori S, 1964, J. Biol. Chem., vol. 55, p. 205–208.
Chemical Abstracts, vol. 80, N°12, XP002110709, 1974.
Chemical Abstracts, vol. 85, N°19, XP002110710, 1976.
Database WPI XP002110711, 1995.
Patent abstracts of Japan (JP 03 137102), 1991.

* cited by examiner

Primary Examiner—Kathleen K. Fonda
Assistant Examiner—Leigh C. Maier
(74) Attorney, Agent, or Firm—Sturm & Fix LLP

(57) ABSTRACT

The subject matter of the invention is branched maltodextrins, characterised by the fact that they present between 22% and 35%, preferably between 27 and 34%, glucosidic linkages 1→6, a content of reducing sugars lower than 20%, a polymolecularity index lower than 5 and a number average molecular weight Mn at most equal to 4500 g/mole, and the method of obtaining these branched maltodextrins.

13 Claims, No Drawings

BRANCHED MALTODEXTRINS AND METHOD OF PREPARING THEM

The subject matter of the invention is branched maltodextrins, hydrogenated or non-hydrogenated, presenting particular characteristics in terms of levels of glucosidic linkages 1→6, of content of reducing sugars, and of average molecular mass.

The invention relates also to a method of manufacturing said branched maltodextrins. It also applies to an acariogenic composition comprising such branched maltodextrins and at least one polyol, which composition may be used in products intended to be ingested by humans or by animals.

In the sense of the invention, by branched maltodextrins is meant maltodextrins, of which the content of glucosidic linkages 1→6 is greater than that of standard maltodextrins.

Standard maltodextrins are defined as purified and concentrated mixtures of glucose and glucose polymers essentially linked in 1→4 with only 4 to 5% glucosidic linkages 1→6, of extremely varied molecular weights, completely soluble in water and with low reducing power.

These standard maltodextrins are conventionally produced by acidic or enzymatic hydrolysis of cereal or tuber starch. The classification of standard maltodextrins is based mainly on the measurement of their reducing power, conventionally expressed by the notion of Dextrose Equivalent or D.E. On this particular point, the definition of maltodextrins repeated in the Monograph Specifications of the Food Chemical Codex states that the D.E. value must not exceed 20.

Such a measurement of the D.E. is, however, insufficient to represent precisely the molecular distribution of standard maltodextrins. Indeed, acidic hydrolysis of starch, totally random, or its enzymatic hydrolysis, slightly more ordered, provides mixtures of glucose and of glucose polymers which the D.E. measurement alone cannot define with precision, and which includes short molecules with a low degree of polymerisation (D.P.), as well as very long molecules with a high D.P.

The D.E. measurement in fact only gives an approximate idea of the average D.P. of the mixture of glucose and of glucose polymers constituting standard maltodextrins, and thus of their number average molecular weight (Mn). To complete the characterisation of the distribution of the molecular weights of the standard maltodextrins, it is important to determine another parameter, that of the weight average molecular weight(Mp).

In practice, the Mn and Mp values are not calculated, but are measured by different techniques. For example, a method of measuring adapted to glucose polymers is used, which is based on gel-permeation chromatography on calibrated chromatographic columns with pullulans of known molecular weights.

The ratio Mp/Mn is called the index of polymolecularity (I.P.) and makes it possible to characterise overall the distribution of the molecular weights of a polymer mixture. As a general rule, the distribution in molecular weights of standard maltodextrins leads to I.P. values of between 5 and 10.

In terms of applications, standard maltodextrins are used in numerous industrial fields and in particular in the food industry.

However, their low rates of branching, their relatively high content of compounds with low D.P. and the fact that no prebiotic effect is attributed to them, means that standard maltodextrins cannot be used in applications for which there is a need to have polyglucosylated compounds with a low calorific value, with low cariogenicity or which improve the quality of the intestinal flora.

By "polyglucosylated compounds with low calorific value" are meant polyglucosylated compounds which, being only slightly assimilated by the human or animal organism, or being only slightly sensitive to the enzymatic activities of the small intestine, do not provide the calorific value of standard polyglucosylated compounds.

By "polyglucosylated compounds with low cariogenicity", are meant compounds which show less acidification by the bacteria of the oral cavity than conventional sugars, such as saccharose, glucose, fructose or standard polyglucosylated compounds. The cariogenic effect is in fact due to the presence, in the oral cavity, of bacteria which metabolise the sugars and cause the production of acids. Lowering the pH of the mouth leads to dissolving the hydroxyapatite of the dental enamel and the creation of cavities.

By "improving the quality of the intestinal flora", is meant promoting the development in the large intestine of micro-organisms which are beneficial to the health of humans or animals, such as bifidogenic, butyrogenic, lactic flora. In this case, there will be talk of prebiotic effect, because improving the development of such a collection of populations of microorganisms which are beneficial to health.

From the above it is apparent that there exists a non satisfied need for having maltodextrins, which as well as their usual properties, have low calorific value, are of low cariogenicity and have the capacity to improve the quality of the intestinal micro-flora.

The Applicant Company had the merit of reconciling all these objectives, previously considered irreconcilable, by devising and developing, at the price of extensive research, new types of products i.e. specific branched maltodextrins.

The branched maltodextrins according to the invention are thus characterised by the fact that they present between 22 and 35%, preferably between 27 and 34%, glucosidic linkages 1→6, a content of reducing sugars lower than 20%, a polymolecularity index lower than 5 and a number molecular weight Mn at most equal to 4500 g/mole.

In practice, the Mn is generally between 250 and 4500 g/mole.

The content of glucosidic linkages 1→6, of between 22 and 35%, gives the branched maltodextrins according to the invention a character of indigestibility, the consequence of which is to reduce their calorific value by preventing their assimilation at the level of the small intestine. Their low content of molecules with a low D.P. such as D.P.1, also contributes to the branched maltodextrins according to the invention presenting a lower calorific value than standard maltodextrins, the quantity of free glucose directly assimilable by the organism being thus greatly reduced. Determining the calorific value of the branched maltodextrins is done by calculation, on the basis of the evaluation of the portion represented by the indigestible fraction in the small intestine and fermented in the large intestine, considered here as providing 2 kcal/g. The branched maltodextrins according to the invention thus have a deduced calorific value lower than 2.5 kcal/g.

The high content of glucosidic linkages 1→6 results in lowering the cariogenic power of the branched maltodextrins according to the invention, by reducing their assimilation by the micro-organisms of the oral cavity.

This high level of glucosidic linkages 1→6 also gives these branched maltodextrins completely specific prebiotic properties. In fact, it has appeared that the bacteria of the caecum and of the colon of humans and animals, such as butyrogenic, lactic or propionic bacteria, metabolise these highly branched compounds.

On the other hand, the branched maltodextrins according to the invention improve the development of bacteria of the bifidogen type to the detriment of the undesirable bacteria. Determining the prebiotic effects of the branched maltodextrins is carried out on animals by the following protocol, perfected by the Applicant Company.

A group of animals, preferably laboratory animals (golden hamsters of the RJ Aura stock) is fed with a solution including 15% by weight/volume of products to be tested. Another control group receives a standard diet. The test is carried out over 14 days, at the end of which the animals are slaughtered and the caecum is removed. The content of acetic, propionic, butyric and lactic acids, which illustrates the development of the corresponding intestinal micro-flora, is determined on the supernatant of a preparation of the contents of the caecum after centrifugation. The analyses carried out after the assimilation of hydrogenated branched maltodextrins with high molecular weights according to the invention have, for example, shown a remarkable development of the intestinal micro-flora.

The branched maltodextrins according to the invention present, furthermore, a content of residual glucosidic linkages 1→4 which is relatively high and a low reducing power which makes it possible for them to retain the same basic functionalities as standard maltodextrins. This content of clucosidic linkages 1→4 can be between 42 and 50%, a content which, to the knowledge of the Applicant Company, has not so far been described in combination with a content of glucosidic linkages 1→6 of between 22 and 35% according to the invention. In a preferential manner, the branched maltodextrins according to the invention present a ratio of glucosidic linkages 1→4/1→6 of between 1.2 and 2.3, and particularly between 1.3 and 2. Branched maltodextrins presenting a ratio of between 1.3 and 1.8 are exemplified below. They can thus play the role of texturizing agents, thickening and/or gelling agents, filling or encapsulating agents, particularly in food products, in pharmaceutical or veterinary products.

Finally, branched maltodextrins according to the invention present an I.P., which being kept at a value lower than 5 makes it possible to define a population of glucose polymers with low dispersion of molecular weights, whilst offering a range of satisfactory molecular weights, since the Mn values can reach 4500 g/mole. This value of the I.P. can be in particular between 1.5 and 3, and for example between 1.8 and 2.9.

A first family of products according to the invention is constituted by branched maltodextrins with high molecular weights, which present by preference a content of reducing sugars at most equal to 5% and an Mn of between 2000 and 4500 g/mole.

In this family, it is possible to distinguish a first sub-family constituted by branched maltodextrins with high molecular weights which present a content of reducing sugars which is lower than 2% and an Mn of between 3000 and 4500 g/mole.

A second sub-family is constituted by branched maltodextrins with high molecular weights which present a content of reducing sugars of between 2% and 5% and an Mn of between 2000 and 3000 g/mole.

A second family of products according to the invention is constituted by branched maltodextrins with low molecular weights, which present preferably a content of reducing sugars of between 5 and 20% and an Mn lower than 2000 g/mole.

In this second family, it is possible to distinguish a first sub-family constituted by branched maltodextrins with low molecular weights which present a content of reducing sugars of between more than 5% and 8% and an Mn of between 500 and 1500 g/mole.

A second sub-family is constituted by branched maltodextrins with low molecular weights which present a content of reducing sugars of between more than 8% and 15% and an Mn lower than 500 g/mole.

The invention also relates to branched maltodextrins, such as those presented before, in hydrogenated form. Hydrogenated branched maltodextrins are in particular intended for applications which require products with good thermal stability and in which the presence of reducing sugars is therefore to be avoided.

The invention also relates to an acariogenic composition, characterised in that it comprises maltodextrins according to the invention and at least one polyol. Said polyol is preferably chosen from the group consisting in threitol, erythritol, xylitol, arabitol, ribitol, sorbitol, mannitol, maltitol, maltotriitol, maltotetraitol, lactitol, hydrogenated isomaltulose, glycerine and hydrogenated starch. hydrolysates.

According to an advantageous embodiment of the invention, the acariogenic composition comprises between 30 and 70% by weight branched maltodextrins and between 70 and 30% by weight maltitol, a composition which has particular application in the manufacture of gums and other confectionery.

From their physico-chemical and physiological properties, the branched maltodextrins according to the invention have a certain and immediate interest in particular in the preparation of acariogenic compositions intended to be ingested by humans or animals.

By the expression "compositions intended to be ingested by humans and animals" are meant compositions or products intended to be ingested and administered orally, such as various foodstuffs such as confectionery, pastries, ice creams, pastes to be chewed, chewing gums, drinks, jams, soups, preparations based on milk, yoghurts, cakes, foodstuffs prepared for animals, pharmaceutical products, veterinary, dietetic or hygiene products such as for example elixirs, cough syrups, tablets or pills, hygienic solutions for oral cavity, toothpastes and tooth gels.

To prepare the branched maltodextrins according to the invention, the following succession of stages is carried out consisting of:

a) preparing a dehydrated acidified starch presenting a humidity lower than 5%, preferably lower than or equal to 4%, b) processing the acidified starch thus dehydrated in a reactor of the thin-layer type at a temperature of between 120 and 300° C., preferably between 150 and 200° C., c) collecting, purifying and preferably concentrating the branched derived starch products thus obtained, d) carrying out a molecular fractionation of said branched derived starch products depending on their number average molecular weight in such a way as to obtain the branched maltodextrins.

The first stage of the method according to the invention consists in preparing a dehydrated acidified starch presenting a humidity lower than 5%, preferably lower than or equal to 4%.

The botanic origin of the starch is insignificant. Thus the starch can come from wheat, from maize, from potato, from rice or from manioc. However the use of wheat starch is preferred as in the example below.

The acid used to acidify the starch can be chosen from the group consisting in hydrochloric acid, sulphuric acid, phosphoric acid, nitric acid and citric acid. However, taking into account the fact that citric acid is capable of generating ester links, undesirable because responsible for bitterness, and the fact that handling sulphuric acid raises obvious safety problems, within the framework of the invention the use of hydrochloric acid, phosphoric acid or nitric acid is preferred. The quantity of acid used in the method according to the invention is between 5 and 100 meq H+/kg dry starch, and preferably between 10 and 50 meq H+/kg dry starch. It is important for the distribution of acid in the starch to be as homogeneous as possible.

Different techniques can be implemented for the acidification of the starch, such as continuous or discontinuous acidification, in dry or liquid phase. Nevertheless, if the acidified starch is intended to be used in a method of continuous modification, in the present invention the use of a continuous means of acidification is preferred in order to realise a method which is as continuous as possible, and thus to limit the non-productive operations (loading, unloading, draining).

Once the acidification has been carried out, the starch is dried to a humidity lower than 5% in order to favour subsequently branching or ramifying between molecules. During this drying stage it is advisable also to limit the hydrolysis reactions so as to avoid increasing undesirable reducing sugars.

The Applicant Company was able to highlight the fact that it was necessary to favour, during this stage, drying techniques of the continuous type making it possible to reach the humidity sought, in a dwell time of the order of minutes, of seconds even, and thus to limit the hydrolysis reactions of the starch.

The second stage of the method according to the invention consists in processing the acidified and dehydrated starch in a reactor of the thin-layer continuous type at a temperature of between 120 and 300° C., preferably between 150 and 200° C. By a reactor of the continuous thin-layer type, the Applicant Company means any type of reactor which makes it possible to apply to the product a very high temperature during a very short period of time, so as to obtain a significant transformation of the structure of the product, mainly at the level of the glucosidic linkages, whilst simultaneously generating as few degradation products as possible. The reactors of the turbo dryer type (for example marketed by the company VOMM) or of the blender type (for example marketed by the Society BUSS) correspond to this definition.

Advantageously, this reactor of the thin-layer continuous type is constituted by a reaction zone kept at a temperature of between 150 and 200° C. The heating can be provided by convection, conduction or radiation. Possibly, this reaction zone can be preceded and/or followed by a conveying zone.

The dwell time for the dehydrated acidified starch in this reactor of the thin-layer continuous type is a function of the temperature and the quantity of acid used during the acidification stage. Processing at high temperature in these conditions and in a very short period of time, which generally does not exceed ten or so seconds, leads to obtaining compounds derived from starch which are very partially hydrolysed and above all enriched with glucosidic linkages 1→6 resulting from branching reactions.

The third stage of the method according to the invention consists in collecting, purifying and preferably concentrating the branched derived starch products thus obtained. The branched derived starch products are collected as they leave the reactor and the conventional purification stages are implemented in order to eliminate the impurities of proteic, lipidic nature, even colouring matter. This purification is carried out by any method which is known per se by the person skilled in the art, for example by filtration, by processing with black, by bleaching and demineralisation on resins or indeed by ultra-filtration. The filtration can be carried out twice, under vacuum, with the aid of a rotary filter under vacuum, and under pressure with the aid of a filter under pressure.

The bleaching can follow the conventional sequence on adsorbent non-functionalised ROHM and HAAS (type XAD 16) resins and on cationic Purolite resins (type C 145) and anionic Purolite resins (type A 860). Then the branched derived starch products, filtered and bleached, can be concentrated by any technique known per se, for example by evaporation.

The branched derived starch products are then submitted to molecular fractionation, then possibly to catalytic hydrogenation. It is also possible to reverse the order of these two stages. This stage of molecular fractionation can consist, for example, in chromatographic separation, in membrane separation or in selective precipitation by means of a solvent.

This stage of molecular fractionation is intended to collect the fractions of branched maltodextrins which present characteristics able to be adapted to a given application, in terms of reduced calorific value, low cariogenicity or prebiotic properties.

Thus, investigations made by the Applicant Company have made it possible to show that, for the manufacture of gums, the fraction of branched maltodextrins presenting an Mn of between 2000 and 4000 g/mole gave very good results.

As a general rule, the molecular fractionation is carried out on branched derived starch products which have been filtered and then demineralised, and concentrated to a dry matter practically of between 20 and 70%, preferably between 25 and 60%.

When one proceeds to this molecular fractionation by the chromatographic route, the stage of chromatographic fractionation is carried out in a manner known per se, either discontinuously or continuously (simulated moving bed) on strong cationic resins of the macroporous type, charged preferably with alkaline and alkaline earth ions, such as calcium and magnesium but more preferably with sodium or potassium ions.

According to a preferred embodiment, the chromatographic fractionation is carried out using the methods and equipment described in the U.S. Pat. No. 4,422,881 of which the Applicant Company is the proprietor. Branched maltodextrins are thus advantageously obtained by passing branched derived starch products on a polystyrene/dyvinyl benzene (or DVB) resin of the strong cationic macroporous type, in the form of potassium with a particle size of 250–300 µm. The strong cationic macroporous polystyrene resin, in the form of potassium, is selected by preference from the group consisting in Purolite C 141 with 5% DVB, or Purolite C 145 with 8% DVB, or Purolite C 150 with 12% DVB.

Generally speaking, the chromatography is carried out on 4 to 10 trays kept at a temperature of the order of 80° C. and supplied with a syrup of branched derived starch products taken to a value of approximately 50% dry matter.

The choice of parameters for carrying out the chromatographic fractionation is understandable to the person skilled in the art. The choice of these parameters is made in such a way that the fraction containing the branched maltodextrins has an Mn and a content of linkages 1→6 according to the invention.

If it should prove necessary, the branched maltodextrins according to the invention can, at this stage of the method, be submitted to a supplementary stage of eliminating the glucose. This supplementary processing to eliminate the glucose can be undertaken if the limited content of free residual glucose of the branched maltodextrins proves to be still undesirable for the applications envisaged. This supplementary processing will be used for example in a case where a low calorific value is sought for the branched maltodextrins, which is the case for maltodextrins with low molecular weights.

This supplementary processing is carried out by any means known per se, for example by transformation of the glucose followed by a stage of desacidification on an anion exchanger. This supplementary stage can be carried out by biological transformation of the glucose by enzymatic oxidation, or with the aid of an oxidising bacterium, or by separation of the glucose on resin or membrane. It can also be carried out with the aid of yeasts which transform the glucose into alcohol which is then eliminated by evaporation in a later stage of the process.

In a variant of the method according to the invention, the branched maltodextrins are subjected to a stage of catalytic hydrogenation. The catalytic hydrogenation of these branched maltodextrins is carried out according to the rules of the art.

The analytic parameters of each of the branched maltodextrins are then determined. More particularly, the content of reducing sugars, expressed in glucose, by weight in relation to the dry weight of the analysed product, is determined by the BERTRAND method. The Mn and Mw values are then measured by steric exclusion chromatography, based on the selective retention of the molecules of the solute depending on their size, by virtue of their penetration or non-penetration into the pores of the stationary phase. The content of glucosidic linkages 1→2, 1→3, 1→4 and 1→6 is determined by using the conventional methylation technique described in HAKOMORI, S., 1964, J. Biol. Chem., 55, 205.

Other characteristics and advantages of the invention will appear more clearly in reading the examples which follow. They are, however, only given here by way of non-restrictive illustration.

EXAMPLE 1

Wheat starch is acidified by hydrochloric acid on the basis of 19.6 meq H+/kg dry, then dried to a residual humidity of 4%. This first matter is then introduced into a BUSS blender of the PR46 type kept at a temperature of 180° C., at a flow rate of 20 kg/h, with a dwell time of 5 seconds. The reaction is stopped quickly by spraying with cold water at 15° C.

After purification by filtration, bleaching on adsorbent resins and on cationic and anionic resins, the branched derived starch products thus obtained are restored to a dry matter of 50%.

The product obtained is submitted to chromatography on strong cationic macroporous resin of Purolite C 145 in the form of potassium, with a particle size of 250–350 μm, laid out in 6 200-liter trays kept at 75° C.

The feed rates of the syrup of branched derived starch products and of the elution water are fixed at 60 l/h and 400 l/h, at the level of the first and third trays respectively. The choice of outflow rates of the second tray and the fourth tray affects whether fractions of branched maltodextrins with high molecular weight or with low molecular weight are obtained.

The outflow rate of the second tray is fixed at 280 l/h in order to obtain compound A and at 320 l/h in order to obtain compound B. The outflow rate of the fourth tray is fixed at 180 l/h for compound C.

The analysis results, after chromatography, are grouped together in the following table I. By way of comparison, certain analytic parameters of standard maltodextrins of prior art are also grouped together, the Mn of which is equivalent to certain branched maltodextrins (compounds D and E).

TABLE I

| PRODUCTS | A | B | C | D | E |
|---|---|---|---|---|---|
| Reducing sugars (%) | 1.75 | 2.3 | 7.2 | 5.7 | 18.2 |
| Mn (g/mole) | 3700 | 2480 | 990 | 3480 | 1140 |
| Mw (g/mole) | 5950 | 5160 | 2200 | 33075 | 10240 |
| I.P. | 1.6 | 2.1 | 2.2 | 9.5 | 9 |
| Linkage 1.2 (%) | 11 | 10 | 10 | 0 | 0 |
| Linkage 1.3 (%) | 13 | 12 | 10 | 0 | 0 |
| Linkage 1.4 (%) | 48 | 49 | 50 | 95 | 95 |
| Linkage 1.6 (%) | 28 | 29 | 30 | 5 | 5 |

EXAMPLE 2

The first stages of preparing the branched maltodextrin according to the invention are the same as those described in Example 1.

Isolating the fraction of low molecular weight is carried out at the level of the fourth tray with an outflow rate fixed at 140 l/h. The fraction with an Mn of 370 g/mole is obtained with an adjustment of the chromatographic parameters which fixes the yield at 30%. The yield here means the proportion of dry matter extracted from this fraction of high molecular weight in relation to the dry matter introduced into the chromatographic system.

The high content of reducing sugars (greater than 20%) has affected the implementation of a stage of eliminating glucose, consisting in a stage of eliminating glucose by glucose oxidase in the following conditions: the solution adjusted to 20% dry matter, pH 6.0 and heated to 35° C. is added with Novozym 771 (NOVO glucose oxidase) at the rate of 1 ml per liter of solution that is 0.5%/dry; kept under agitation at 750 μm and an aeration of 1.2 vvm, the solution containing initially 13%/dry glucose, after 5 hours titrates less than 10%/dry. The analytic results of the resulting branched maltodextrin F according to the invention are group ether in table II.

TABLE II

| PRODUCTS | F |
|---|---|
| Reducing sugars (%) | 9.9 |
| Mn (g/mole) | 380 |
| Mw (g/mole) | 755 |
| I.P. | 2 |
| Free glucose (%/dry) | <1 |
| Linkage 1, 2 (%) | 11 |
| Linkage 1, 3 (%) | 12 |
| Linkage 1, 4 (%) | 44 |
| Linkage 1, 6 (%) | 33 |

EXAMPLE 3

Gums are manufactured from a mixture M of 50% by weight branched maltodextrins according to the invention corresponding to product B of Example 1 with 50% by weight maltitol.

The formula of the gums is given in the following table III.

TABLE III

| FORMULA | Per 100% total |
| --- | --- |
| Mixture M (DM*) | 4.28% |
| Arabic gum (DM*) | 38% |
| Mint | 6.2% |
| Relative humidity | 10% |

*DM.: dry matter

The characteristics of the gums obtained are grouped together in table IV below:

TABLE IV

| GUMS | |
| --- | --- |
| Activity in water at 20% | 0.57 |
| % humidity after 3 days at 75% relative humidity at 20° C. | 3.2% |
| "Sticking" nature after 3 days under relative humidity of 75% at 20° C. | 0/+(a) |
| INSTRON hardness | 31 |
| Hardness estimated by sensorial analysis | +++(b) |

(a) 0: absence of "sticking" nature
+: slight "sticking" nature
(b) hard consistency but absence of brittle nature The behaviour of the gums obtained with the mixture M according to the invention is thus completely advantageous since it is characterised by:
  low hygroscopicity, which is shown as a very low water regain (particularly with an activity in water lower than 3.5) when these gums are placed in a humid atmosphere,
  an in-mouth texture, and an INSTRON hardness (between 25 and 35), making it possible to use a smaller quantity of arabic gum, whence an appreciable financial saving.

It emerges from the above that the use of the branched maltodextrins and of the compositions according to the invention is particularly adapted to the preparation of confectionery, and particularly gums.

To the knowledge of the applicant company, gums based on branched maltodextrins have never been described, which present simultaneously the two characteristics quoted above of water regain and INSTRON hardness.

What is claimed is:

1. Branched maltodextrins, presenting between 22% and 35% glucosidic linkages 1→6, a content of reducing sugars lower than 20%, a polymolecularity index lower than 5 and a number average molecular weight Mn at most equal to 4500 g/mole.

2. Branched maltodextrins according to claim 1, presenting between 27 and 34% glucosidic linkages 1→6.

3. Branched maltodextrins according to claim 1, presenting a content of reducing sugars lower than 2% and an Mn of between 3000 and 4500 g/mole.

4. Branched maltodextrins according to claim 1, presenting a content of reducing sugars of between 2% and 5% and an Mn of between 2000 and 3000 g/mole.

5. Branched maltodextrins according to claim 1, presenting a content of reducing sugars greater than 5% and at most equal to 8%, and an Mn of between 500 and 1500 g/mole.

6. Branched maltodextrins according to claim 1, presenting a content of reducing sugars greater than 8% and at most equal to 15% and an Mn lower than 500 g/mole.

7. Branched maltodextrins according to claim 1, wherein they are hydrogenated.

8. Composition of low cariogenicity, which comprises branched maltodextrins according to claim 1, and at least one polyol.

9. Composition of low cariogenicity according to claim 8, which comprises between 30 and 70% by weight branched maltodextrins, and between 70 and 30% by weight maltitol.

10. Method of preparing branched maltodextrins according to claim 1, in which:
  a) a dehydrated acidified starch is prepared presenting a humidity lower than 5%,
  b) the acidified starch thus dehydrated is processed in a reactor of the thin-layer continuous type, at a temperature of between 120 and 300° C., for a period of time that does not exceed about ten seconds,
  c) the branched derived starch products thus obtained are collected, purified and preferably concentrated,
  d) the branched derived starch products are molecular fractionated depending on their number average molecular weight on a macroporous resin, in such a way as to obtain the branched maltodextrins.

11. Method according to claim 10, wherein said temperature is between 150 and 200° C.

12. Method according to claim 10, wherein in said step a), a dehydrated acidified starch is prepared presenting a humidity lower than or equal to 4%.

13. Method according to claim 10, wherein a catalytic hydrogenation of the branched maltodextrins according to the invention is carried out.

* * * * *